Feb. 3 , 1953 M. R. JACOBUS Plant Pat. 1,163

ROSE PLANT

Filed Jan. 2, 1952 2 SHEETS—SHEET 1

Inventor.
M. R. Jacobus
By Robert Cobb
Attorneys.

Inventor.
M. R. Jacobus
By: Robb & Robb
Attorneys.

Patented Feb. 3, 1953

Plant Pat. 1,163

UNITED STATES PATENT OFFICE 1,163

ROSE PLANT

Martin R. Jacobus, Ridgefield, N. J., assignor to Bobbink & Atkins, East Rutherford, N. J., a corporation of New Jersey Application January 2, 1952, Serial No. 264,532

1 Claim. (Cl. 47—61)

Figure 1:
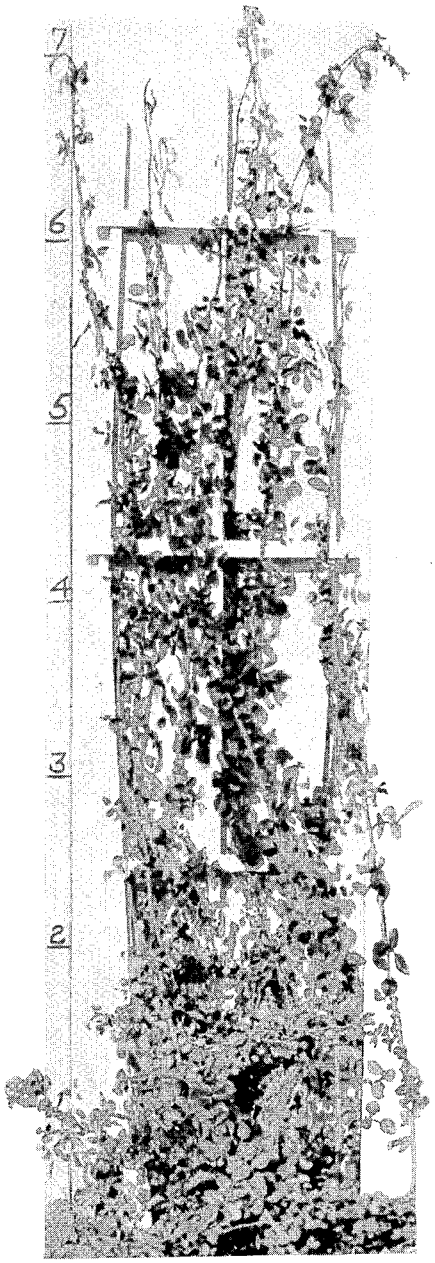

The present invention relates to a new and distinct variety of rose plant of the everblooming climber type, originated by me by crossing the variety "Dream Girl" (Plant Patent No. 643) with an unnamed and unpatented variety of unidentified origin.

As the result of this cross, I have produced a new variety which is dominantly characterized as to novelty by the following unique combination of distinctive features which distinguish it from its parents, as well as from all other varieties:

(1) Strong everblooming characteristic and consequent production of a good crop of flowers in the month of June, another crop in the month of August, and again during October and November, depending upon the lateness of the fall season;

(2) Extreme hardiness and ruggedness of the plant constitution;

(3) Vigorous growth, resulting in the production of runners from maiden plants as long as 6 to 7 feet in the nursery rows, said runners and branches being winter-hardy, with little or no injury by frost;

(4) Long-lasting quality of the blooms, both on the plants and as cut flowers;

(5) Abundance of dark green, mildew-resistant foliage as a background for the white flowers, giving the general effect of extreme floriferousness, especially when many of the blooms are borne in clusters during mid-summer; and (6) The predominant white color of the blooms, which at certain times are delicately tinted lemon-yellow, but eventually change to white.

My new variety somewhat resembles the old climbing rose known as "Gardenia" (unpatented), particularly in respect to its foliage, but this old variety is not of the everblooming type, and even though its individual blooms are not as large as those of my new variety, the variety "Gardenia" was and still is held in high esteem. To the best of my knowledge, my new variety is the first and only true everblooming white rose of the climber class.

Asexual reproduction of the new variety by budding at Ridgefield, New Jersey, shows that the foregoing characteristics and distinctions come true to form and are established and transmitted through succeeding propagations.

Figure 2:
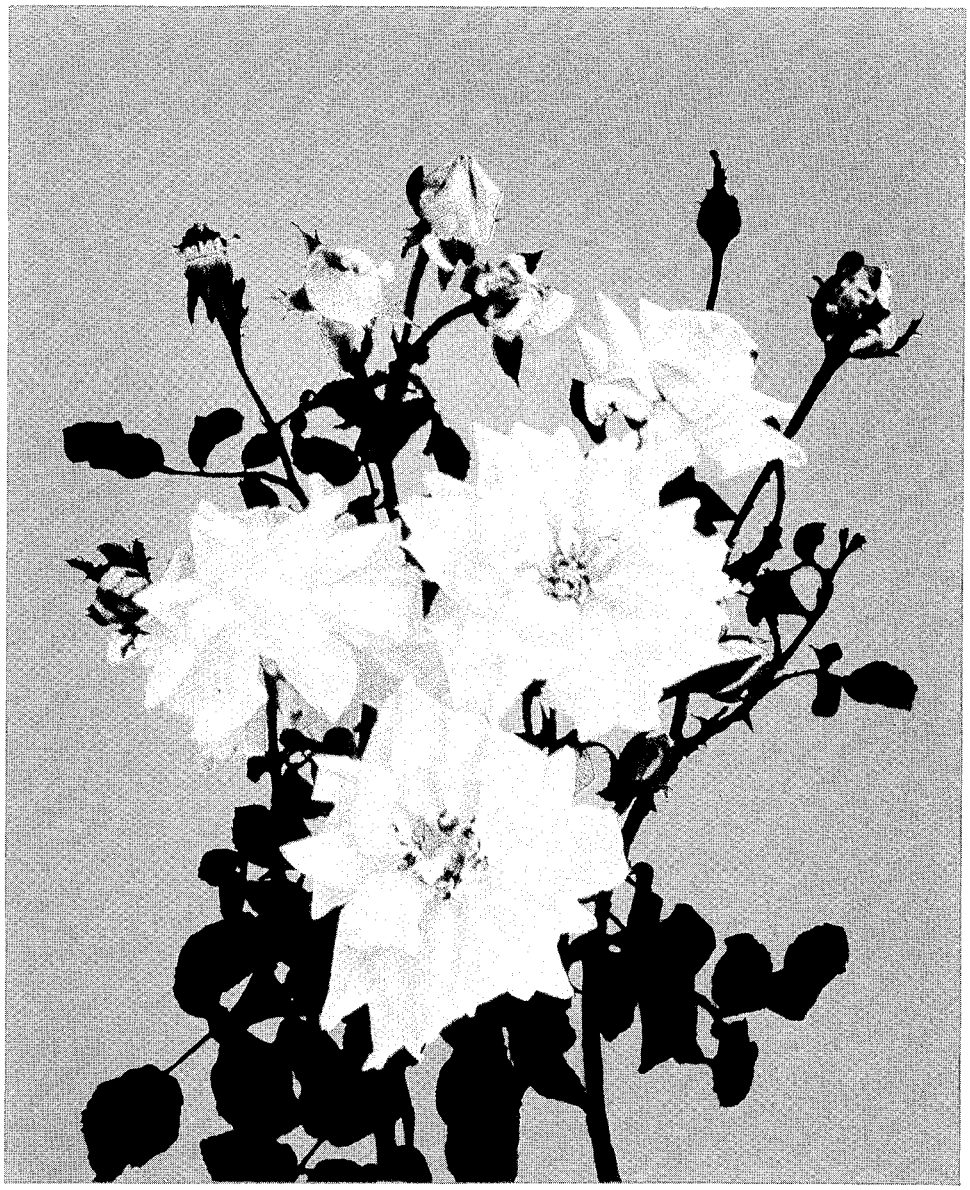

In the drawings:

Fig. 1 shows a specimen plant of the new variety in black-and-white, which is illustrative of its typical climbing habit of growth, as indicated by the scale marked in feet beside the plant; and Fig. 2 shows specimens of the flowers and foliage in color on a slightly enlarged scale, with the flowers and foliage in different stages of development.

The following is a detailed description of the new variety, with color terminology in accordance with Ridgway's Color Standards and Nomenclature, except where general color terms of ordinary dictionary significance are obvious:

Type: Hardy; climbing; outdoor; seedling; for garden decoration.

Class: Hybrid Wichuraiana.

Breeding: Seedling.

*Seed parent.*—"Dream Girl."

*Pollen parent.*—An unnamed variety of unidentified origin.

Propagation: Holds its distinguishing characteristics through succeeding propagations by budding.

*Flower*

Locality where grown and observed: Ridgefield, New Jersey.

Continuity: Intermittent.

Fragrance: Moderate.

Flowers borne: Several to stem; sometimes in clusters; on strong, medium length stems.

Quantity of bloom: Abundant, outdoors.

Bud:

*Peduncle.*—Medium length; heavy; erect; medium smoothness; few red prickles. Color—Yellow Oil Green, Plate V, 25, k, with edges Etruscan Red, Plate XXVII, 5, —.

*Before calyx breaks.*—Size—small. Form—short; pointed; with slender, much cut foliaceous parts extending beyond the tip of the bud equal to one-half of its length. Color—Cerro Green, Plate V, 27, m.

*As calyx breaks.* — Color — Glass Green, Plate XXXI, 29, d, blushed with Jasper Red, Plate XIII, 3, —.

*As first petal opens.* — Size — small. Form—ovoid. Color — outside — Glass Green, Plate XXXI, 29, d, blending into Pale Glass Green, Plate XXXI, 29, f, blushed with Eugenia Red, Plate XIII, 1, —; inside—Pale Glass Green, Plates XXXI, 29, f, blending into white. Opening—opens up well. Is retarded from opening by cold weather.

Bloom:

*Size.*—When fully open—medium; 2¾ inches to 3¼ inches.

*Petalage.*—Double; from 45 to 50 petals; arranged irregularly.

*Form.*—High center; globular at first; becoming flat, open-centered; petals being at first tightly rolled outward; becoming later, at maturity, flat and loosely rolled outward.

Petals: Soft, with inside and outside satiny.

*Shape.*—Outside — ovate with apex having two notches. Intermediate — oval with apex formed with two notches. Inside—lanceolate with apex formed with two notches.

This description of a newly opened flower was made from a rose grown outdoors in the month of July, at East Rutherford, New Jersey:

*Color.* — Outside petal — outside surface: White (depth color), overlaid with Baryta Yellow, Plate IV, 21, f; inside surface: White (depth color), overlaid with Baryta Yellow, Plate IV, 21, f. Intermediate petal—outside surface: White (depth color), overlaid with Pinard Yellow, Plate IV, 21, d; inside surface: White (depth color), overlaid with Pinard Yellow, Plate IV, 21, d. Inner petal—outside surface: Sulphur Yellow, Plate V, 25, f (depth color), overlaid with Pinard Yellow, Plate IV, 21, d; inside surface: Sulphur Yellow, Plate V, 25, f (depth color), overlaid with Pinard Yellow, Plate IV, 21, d.

This description was made from a rose that was open for three days indoors in the month of July, at East Rutherford, New Jersey:

*Color.* — Outside petal — outside surface: White (depth color), overlaid with Sulphur Yellow, Plate V, 25, f; inside surface: White (depth color), overlaid with Sulphur Yellow, Plate V, 25, f. Inside petal—outside surface: White (depth color), overlaid with Martius Yellow, Plate IV, 23, f; inside surface: White (depth color), overlaid with Martius Yellow, Plate IV, 23, f.

*General color effect.*—Newly opened flower—White. Three days open—White.

*Behavior.*—Drop off cleanly.

*Flower longevity.*—On bush in garden — 5 days in June. Cut roses grown outdoors, kept at living room temperatures—4 days in June.

*Reproductive organs*

Stamens: Medium number; arranged irregularly; mixed with petaloids. Color—Aniline Yellow, Plate IV, 19, i.

Filaments: Short; few with anthers. Color—Sulphur Yellow, Plate V, 25, f.

Anthers: Small; open at various times. Color—Apricot Yellow, Plate IV, 19, b.

Pollen: Very sparse. Color—Light Cadmium, Plate IV, 19, —.

Pistils: Few.

Styles: Uneven; short; thin; bunched. Color—Pale Viridine Yellow, Plate V, 29, f.

Stigma: Color—Pale Green-Yellow, Plate V, 27, f.

Ovaries: All enclosed in calyx. Color—Peacock Green, Plate VI, 35, i, shaded Cedar Green, Plate VI, 31, m.

Hips: Short; globular; smooth; walls thick, fleshy. Color—Russet.

Sepals: Permanent; short; spear-shaped. Color—Grass Green, Plate VI, 33, k, with a touch of Pinkish Vinaceous, Plate XXVII, 5, d.

Seeds: Very few; small.

*Plant*

Foliage:

*Leaves.*—Compound of five leaflets; normal abundance; medium size; moderately heavy; glossy; wrinkled.

*Leaflets.*—Shape—oval with apex acute. Base—round. Margin—Simply serrate.

*Color.*—Mature—upper surface: Forest Green, Plate XVII, 29, m; under surface: Parrot Green, Plate VI, 31, k. Young—upper surface: Light Cress Green, Plate XXXI, 29, i; under surface—edges Rainette Green, Plate XXXI, 27, i, and lightly blending to Oxblood Red, Plate I, 1, k, center.

*Rachis.*—Medium weight. Upper side—smooth. Under side—sparsely prickly.

*Stipules.*—Very short; narrow; with short points, turning out at an angle of 90°; recurved toward the stem.

*Disease.*—Resistant to mildew, as determined by comparison with other varieties of the same class grown under comparable conditions at Ridgefield, New Jersey.

Growth:

*Habit.*—Climbing.

*Growth.*—Vigorous.

*Canes.*—Heavy.

*Main stems.*—Color—Dull Green-Bronze. Thorns—several; medium length; straight; with long, narrow base. Prickles—few; color—Bronze. Hairs—few; color—Green.

*Branches.*—Color—Dull Green. Thorns—several; medium length; straight; with short, narrow base. Prickles—few; color—reddish. Hairs—few; color—Green.

*New shoots.*—Color — Bright Green. Thorns—several; medium length; straight; with short, narrow base. Prickles—few; color—reddish. Hairs—few; color—Green.

I claim:

A new and distinct variety of rose plant of the everblooming climber type, substantially as herein shown and described, characterized as to novelty particularly by its extremely hardy, rugged, vigorous and everblooming habits of growth, by the long-lasting quality of its blooms and the general effect of extreme floriferousness thereof against a background of dark green, mildew-resistant foliage, and by the predominant white color of its blooms, sometimes tinted with lemon-yellow color, but eventually changing to white.

MARTIN R. JACOBUS.

No references cited.